United States Patent
Gastrock et al.

[11] 4,075,228
[45] Feb. 21, 1978

[54] 1,3-DITHIOLANE COMPOUNDS AND METHOD OF PREPARATION THEREOF

[75] Inventors: William Henry Gastrock, Hightstown; Goro Asato, Titusville, both of N.J.

[73] Assignee: American Cyanamid Company, Stamford, Conn.

[21] Appl. No.: 720,163

[22] Filed: Sept. 2, 1976

Related U.S. Application Data

[62] Division of Ser. No. 799,887, May 23, 1977.

[51] Int. Cl.² ............... C07D 333/16; A01N 9/00
[52] U.S. Cl. ............... 260/332.3 P; 260/329 HS; 260/327 A; 260/332.2 R; 424/275; 426/648
[58] Field of Search ............... 260/329 HS, 332.3 R, 260/332.3 P

[56] References Cited
U.S. PATENT DOCUMENTS 3,803,172  4/1974  Van Der Wal ............... 260/329 HS

*Primary Examiner*—Bernard Helfin
*Assistant Examiner*—A. Siegel
*Attorney, Agent, or Firm*—Harry H. Kline

[57] ABSTRACT

There are provided substituted 1,3-dithiolane compounds and a method for preparing the same. Said 1,3-dithiolane compounds are useful intermediates in the preparation of tetrahydro-7-oxobenzo[b]thien-4-ylureas and tetrahydro-4-oxo-1-naphthylureas which are known animal growth-promoting agents, which thiolanes are represented by the formula:

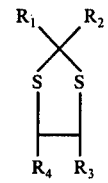

wherein $R_1$ is a member selected from the group consisting of 2-thienyl and phenyl; $R_2$ is a member selected from the group consisting of

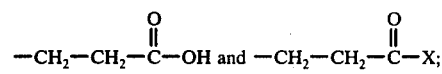

wherein X is chlorine or bromine; $R_3$ and $R_4$ are each members selected from the group consisting of hydrogen and methyl; and when $R_1$ and $R_2$ are taken together with the carbon atom to which they are attached they represent a bicyclic moiety selected from the group consisting of

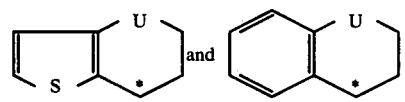

wherein the carbon atom of said bicyclic moiety marked with an asterisk is also part of the 1,3-dithiolane ring; U is a moiety selected from the group consisting of

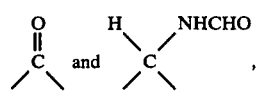

and when U is

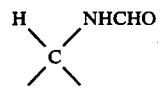

said compounds are the racemic mixtures and the optical isomers thereof.

3 Claims, No Drawings

1,3-DITHIOLANE COMPOUNDS AND METHOD OF PREPARATION THEREOF

This application is a divisional application of Ser. No. 799,887 filed on 5/23/77.

BACKGROUND OF THE INVENTION

The compounds: 4,5,6,7-tetrahydro-7-oxobenzo[b]-thien-4-ylurea of formula (I) and 1,2,3,4-tetrahydro-4-oxo-1-naphthylurea of formula (II):

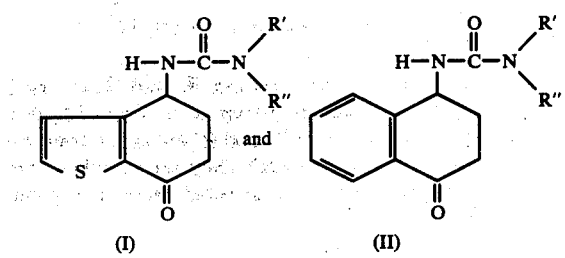

wherein R' and R" are substituents, such as hydrogen, alkoxy, alkyl and benzyl are useful and valuable animal growth-promoting agents. The compounds of formula (I) are disclosed in the German Offenlegungschrift No. 2,501,788 issued July 7, 1975, and are also the subject of an application for U.S. Pat., Ser. No. 532,449, filed Dec. 13, 1974. Compunds of formula (II) are disclosed in an application for U.S. Pat., Ser. No. 582,559, filed May 20, 1975. Both the German Offenlegungshrift and the aforementioned applications are incorporated herein by reference.

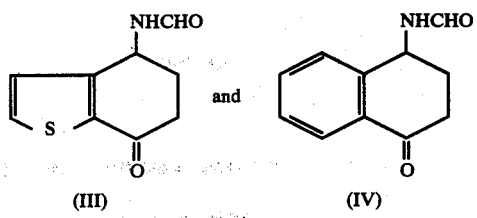

wherein said amides are the racemic mixtures and the optically active isomers thereof, are useful and valuable intermediates for the synthesis of the above urea compounds represented by formulas (I) and (II). In general, the amides of formulas (III) and (IV) are conveniently prepared by oxidation reactions from the corresponding amides of formulas (V) and (VI) as hereinbelow illustrated in the following manner:

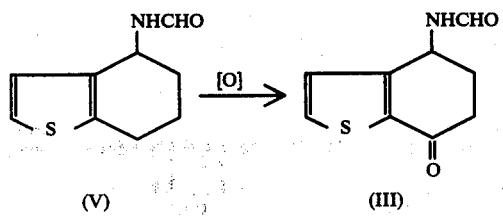

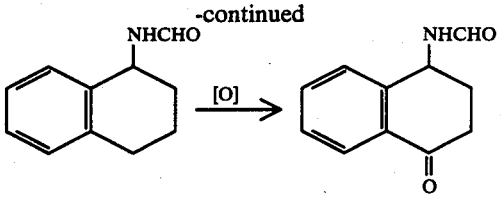

To one equivalent of the amide of formula (V) or (VI) are added from 2 to 8 equivalents and, preferably, from 4 to 5 equivalents of an oxidizing agent, such as a ceric salt, chromic acid, sodium bichromate and equivalents thereof, at a temperature between about 0° and 100° C and, preferably, from 20° to 60° C, in an inert solvent such as an aqueous solution of acetic acid, acetonitrile, tetrahydrofuran, dioxane, dimethoxyethane and the like, which can be admixed with nitric acid, phosphoric acid, perchloric acid.

Alternatively, the amides can initially be treated with an oxidizing agent such as chromic anhydride in acetic anhydride, followed by hydrolysis. Further the amides (V) and (VI) can also be oxidized with oxygen or with a mixture of oxygen and an inert gas at atmospheric or superatmospheric pressures in the presence of a cobalt catalyst selected from any suitable $Co^{+2}$ and $Co^{+3}$ salt, in a solvent selected from lower alkanoic acids, aliphatic or cycloaliphatic ketones, lower alcohols, or mixtures thereof, at a temperature range of 20° to 150° C, and preferably 25° to 120° C.

Each of the above procedures affords desired intermediates [formulas (III) and (IV)] in satisfactory yields. However, the use of metal oxidizing agents is expensive and their recovery from an oxidizing mixture is difficult. Moreover, the use of an oxidant, such as chromic acid in acetic anhydride, can result in the formation of chromyl acetate, a potentially explosive compound. The oxygen/catalyst route also poses a problem, since it employs flammable solvents, some of which (the ketones) may form potentially dangerous peroxides.

Thus, disposal of the effluents, containing the above oxidants, in the environment can have an undesired impact on same, the magnitude of which can not be predicted with any degree of certainty.

It is apparent, therefore, that is a procedure which does not require any oxidation reactions for the preparation of compounds of formulas (III) and (IV) could be devised, such would fulfil a long felt need in the art.

Surprisingly, it has been found that the compounds of the present invention represented by formulae (VII or VIII) are provided which can be converted with ease to the corresponding compounds of formulas (III) and (IV) as hereinbelow graphically illustrated:

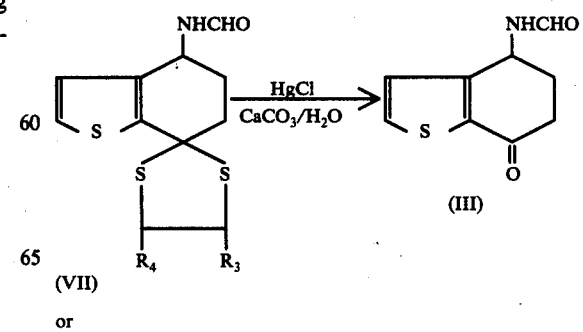

or

-continued

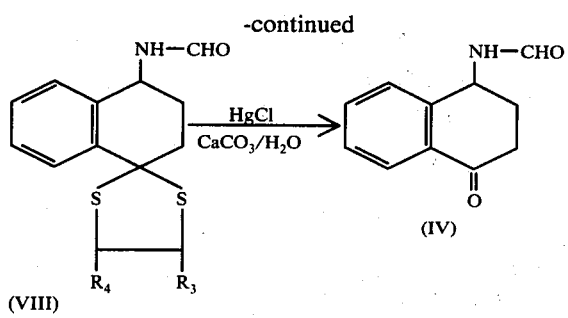

(VIII)

wherein $R_3$ and $R_4$ are each hydrogen or methyl; as well as the racemic mixtures and the optical isomers thereof.

Hydrolysis of the amides of formulas (III) and (IV) yields the corresponding oxo amines of formula (IX) and (X):

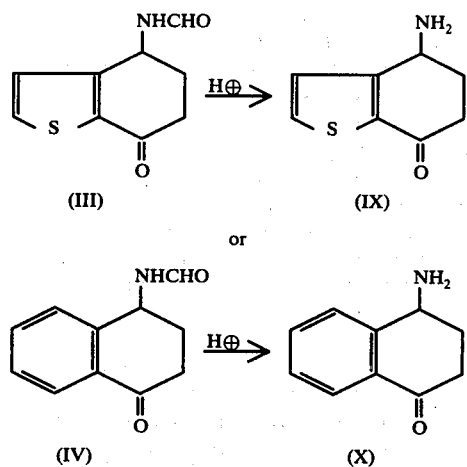

which, when reacted with urea, metal cyanates, alkyl or aryl isocyanates, carbamoyl halides, yield the afore-said animal growth regulating compounds of formulas (I) and (II).

According to the invention, the 1,3-dithiolane compounds are represented by formula (XI) below:

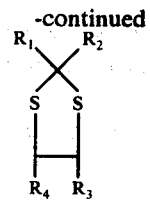

(XI)

-continued

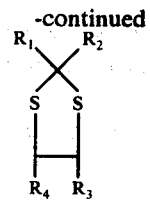

wherein $R_1$ is a member selected from the group consisting of 2-thienyl and phenyl; $R_2$ is a member selected from the group consisting of

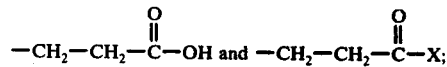

wherein X is chlorine or bromine; $R_3$ and $R_4$ are each members selected from the group consisting of hydrogen and methyl; and when $R_1$ and $R_2$ are taken together with the carbon atom to which they are attached they represent a bicyclic moiety selected from the group consisting of

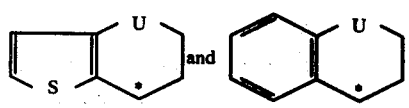

wherein the carbon atom of said bicyclic moiety marked with an asterisk is also part of the 1,3-dithiolane ring; U is a moiety selected from the group consisting of

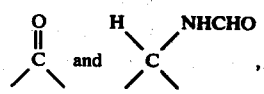

and when U is

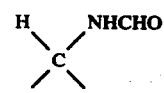

said compounds are the racemic mixtures and the optical isomers thereof.

The reaction sequence leading to the compounds (XI) of the present invention is hereinbelow graphically illustrated by flow diagrams, wherein $R_1$ of formula (XI) hereinabove is either 2-thienyl or phenyl as indicated in Scheme 1. or Scheme 2, respectively.

Flow Diagrams

1. Scheme 1 wherein $R_1$ is 2-thienyl

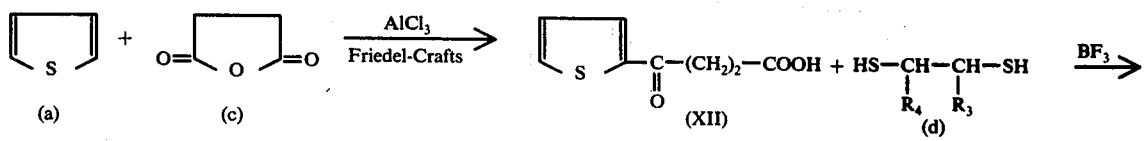

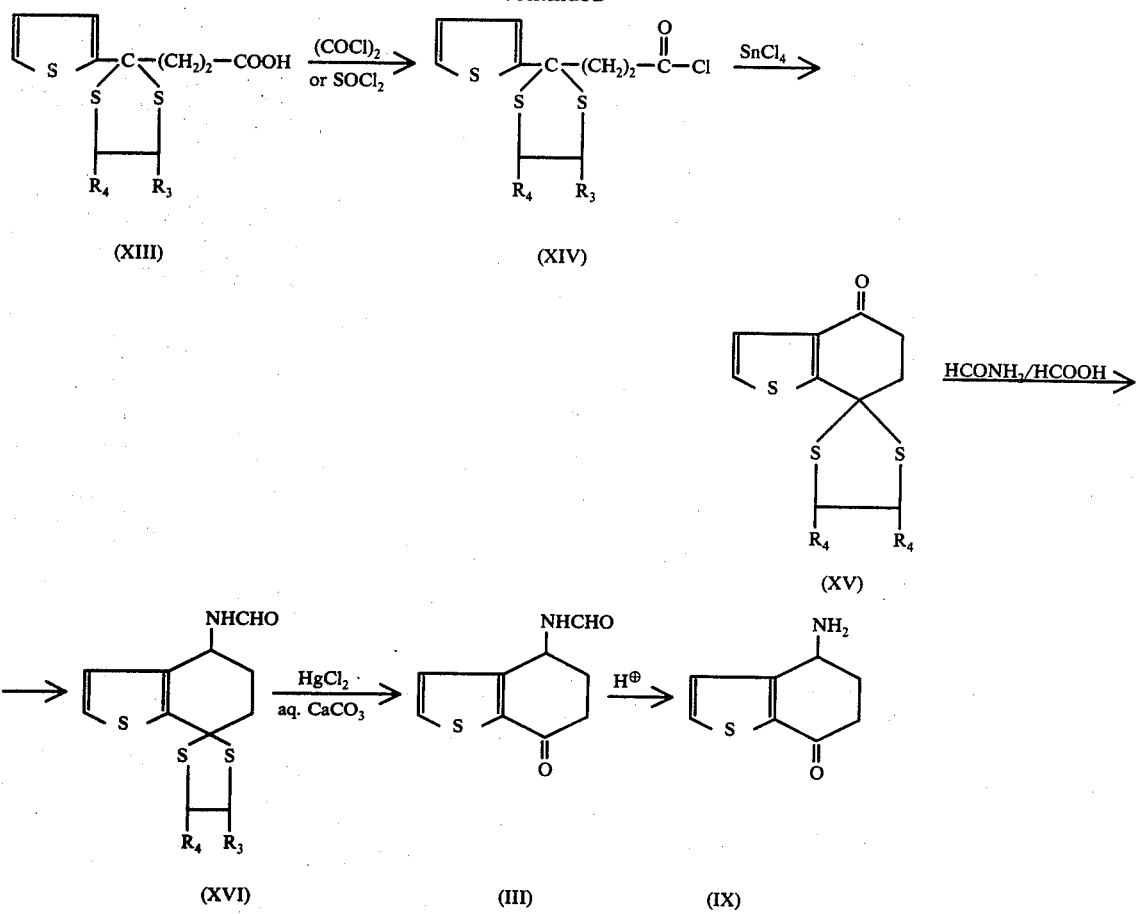
2. Scheme 2 wherein $R_1$ is phenyl
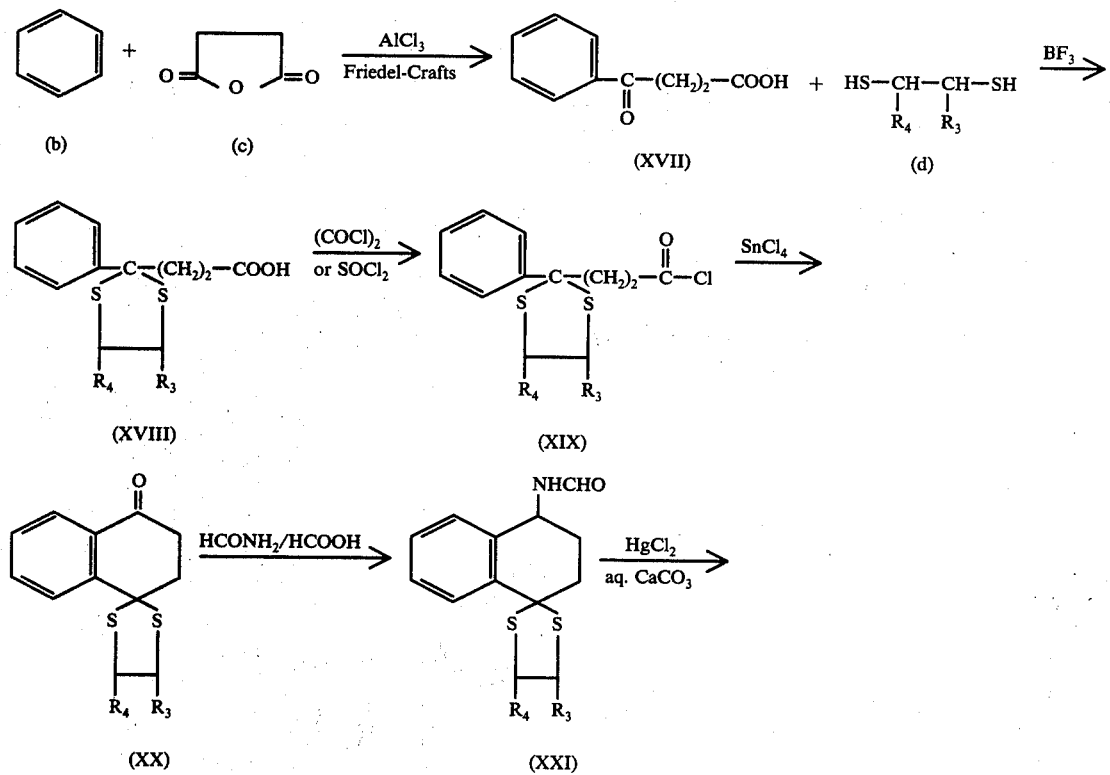

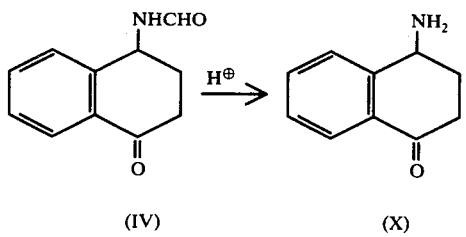

(IV) → (X)

Advantageously, the 1,3-dithiolanes of formula (XI) can alternatively be prepared by the following reaction sequence:

Step 1:

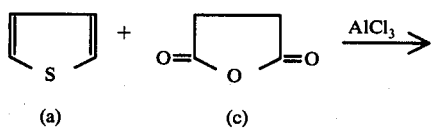

(a) + (c) →(AlCl₃)

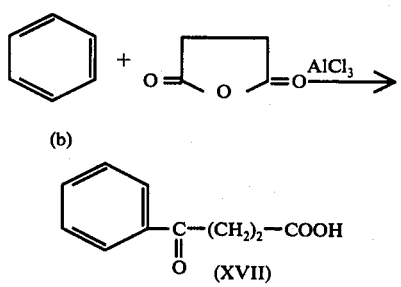

(XII)

or

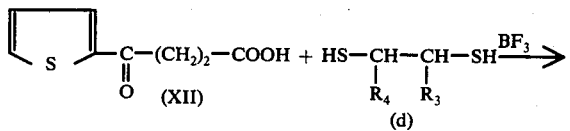

(b)

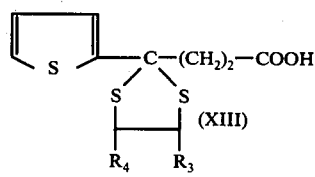

(XVII)

Thiophene (a) is reacted with succinic anhydride (c) under Friedel-Crafts reaction conditions to afford 4-(2-thienyl)-4-oxobutyric acid (XII). Substitution of benzene (b) in the above reaction affords 4-phenyl-4-oxobutyric acid (XVII).

Step 2:

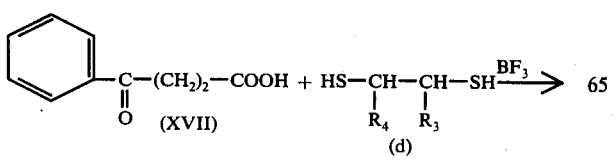

(XII) + (d) →(BF₃)

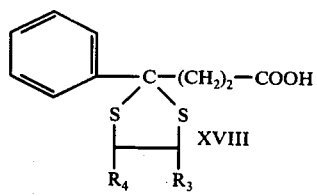

(XIII)

or

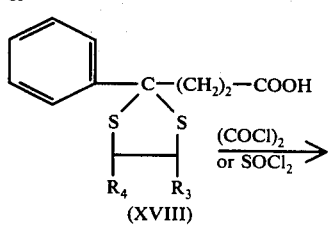

(XVII) + (d) →(BF₃)

XVIII

The oxobutyric acids of formulas (XII) and (XVII) obtained in Step 1 above, are reacted with a suitable 1,2-dithiol (d), R₃ and R₄ are each either hydrogen or methyl, in an aromatic solvent such as benzene, toluene or xylene, in the presence of catalytic amounts of p-toluenesulfonic acid at a temperature range of 25° to 120° C and, preferably, from 75° to 110° C while azeotroping the water formed in the reaction. Alternatively, the reaction is conducted in a C₂-C₅ alkanoic acid, preferably, acetic acid in the presence of an acid catalyst such as boron trifluoride/methanol, boron trifluoride/ether, ZnCl₂/Na₂SO₄, HCl/ether, and the like, at the temperature range specified above, to afford 2-(2-thienyl)-1,3-dithiolanepropionic acid (XIII) and 2-phenyl-1,3-dithiolane-2-propionic acid (XVIII), respectively. R₃ and R₄ are as hereinabove defined.

Step 3:

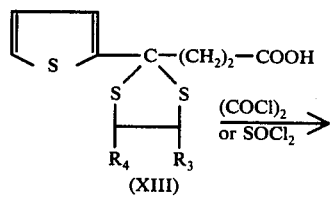

(XIII) →((COCl)₂ or SOCl₂)

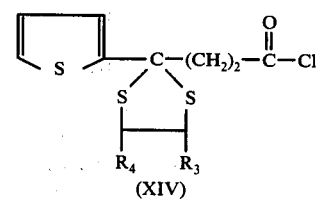

(XIV)

or (XVIII) →((COCl)₂ or SOCl₂)

-continued

[Structure XIX: phenyl-C(S-CHR4-CHR3-S)-(CH2)2-C(=O)-Cl]

The dithiolane propionic acids of formulae (IIIa) and (IIIb) are converted to the corresponding acid chlorides of formulae (XIV) and (XIX) with oxalyl chloride or thionyl chloride (with a small amount of DMF added if desired) in an inert anhydrous solvent selected from the group consisting of benzene, toluene, xylene, chlorobenzene, at a temperature range of about 0° to 30° C and preferably 15° to 30° C.

Step 4

[Structure XIV] + SnCl₄ → [Structure XV: spiro[benzo[b]thiophene-7(6H), 2'-[1,3]dithiolan]-4(5H)-one]

or

[Structure XIX] + SnCl₄ → [Structure XX: spiro[naphthalene-4(3H), 2'-[1,3]dithiolan]-1(2H)-one]

In this reaction step, the acid chlorides of formulae (XIV) and (XIX) are ring closed with stannic chloride in an inert anhydrous solvent such as methylene chloride, ethylene dichloride and the like, at a temperature range of −20° to +20° C preferably 0° to 10° C, to afford spiro[benzo[b]thiophene-7(6H), 2'-[1,3]dithiolan]-4(5H)-one of formula (XV) and spiro[naphthalene-4(3H), 2'-[1,3]dithiolan]-1(2H)-one of formula (XX), respectively, or derivatives thereof wherein $R_3$ and $R_4$ are each hydrogen or methyl.

Step 5

[Structure XV] + HCONH₂/HCOOH $\xrightarrow{\Delta}$

[Structure XVI: N-(5,6-dihydrospiro[benzo[b]thiophen-7(6H), 2'-[1,3-dithiolan]-4-yl)formamide]

or

[Structure XX] + HCONH₂/HCOOH $\xrightarrow{\Delta}$

[Structure XXI: N-(2,3-dihydrospiro[naphthalene-4(3H), 2'-[1,3-dithiolan]-4-yl)formamide]

Conversion of the oxo compounds of formulae (XV) and (XX) to the corresponding formamides is achieved by heating same with an equimolar or excess amount of formamide-formic acid or ammonium formate-formic acid mixture at a temperature of about 150° to 200° C and preferably 150° to 180° C for a period of time about 3 to 8 hours to afford N-(5,6-dihydrospiro[benzo[b]thiophen-7(6H), 2'-[1,3-dithiolan]-4-yl)formamide of formula (XVI) and N-(2,3-dihydrospiro[naphthalene-4(3H), 2'-[1,3-dithiolan]-4-yl)formamide of formula (XXI), respectively, wherein said compounds are the racemmic mixtures and the optical isomers thereof.

The removal of the 1,3-dithiolane group and the simultaneous introduction of an oxo group on the same carbon atom in the compounds of formulae (XVI) and (XXI) is readily accomplished by using mercuric halide, such as mercuric chloride/aqueous calcium carbonate in acetonitrile or acetone, at a temperature range of 20° to 70° C, preferably 20° to 40° C to afford the compounds of formulae (III) and (IV) as hereinbelow graphically illustrated:

[Structure XVI] $\xrightarrow[\text{CH}_3\text{CN; }\Delta]{\text{HgCl}_2/\text{aq. CaCO}_3}$ [Structure III]

-continued

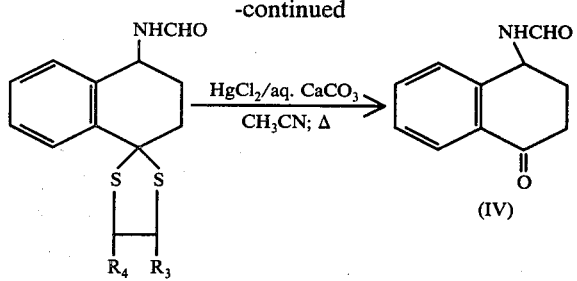
(XXI)

Next, the amides of formulae (III) and (IV) are hydrolyzed with dilute acid or alkali, preferably an acid (e.g. hydrochloric acid) to 4,5,6,7-tetrahydro-7-oxobenzo[b]thiophen-4-amine of formula (IX) and 1,2,3,4-tetrahydro-4-oxo-1-naphthylamine of formula (X), or salts thereof, as hereinbelow graphically illustrated:

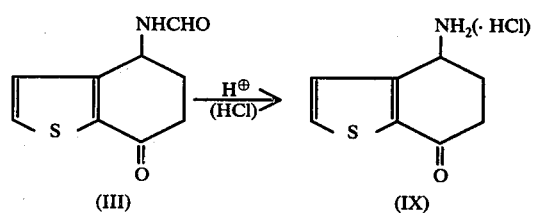

and

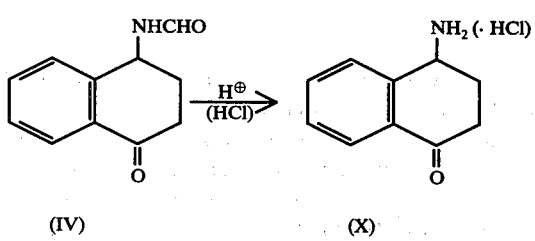

and wherein said oxoamines are the racemic mixtures and the optical isomers thereof.

Formulas (I) and (II) urea compunds, wherein R' and R" are hydrogen, may be advantageously prepared from the above-identified oxoamines (or acid salts thereof) by reacting said amines with approximately equimolar amounts of sodium or potassium cyanate, however it is generally preferable to employ 5 to 50% excess of the cyanate.

The reaction can be conducted at atmospheric or superatmospheric pressure at a temperature in the range of 0° to 100° C, but is preferably conducted at atmospheric pressure at 0° to 70° C in the presence of a solvent selected from water, polar solvents such as $C_1$-$C_3$ alcohols, tetrahydrofuran, dioxane, ethylene glycol dimethyl ether, acetone, methyl ethyl ketone and the like, and mixtures thereof; in the pH range of 5 to 7 and preferably at pH 6. The above reaction may be graphically illustrated as follows:

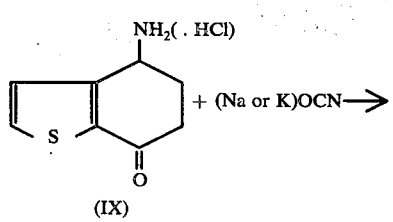

-continued

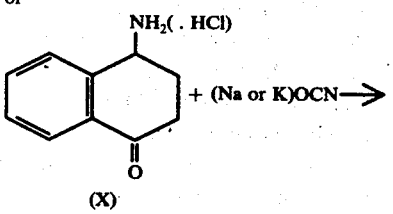
(I)

or

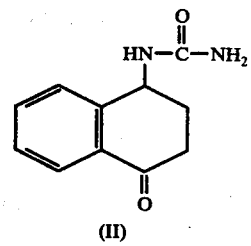

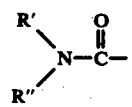
(II)

Substituted ureas of formulae (I) or (II) may be advantageously prepared by treating the above-identified amines of formulae (IX) or (X) with an appropriately substituted alkyl isocyanate of formula: R'—NCO or with a carbamoyl halide of formula:

$$\begin{array}{c} R' \\ \diagdown \\ N-C- \\ \diagup \quad \| \\ R'' \quad O \end{array}$$

halide, wherein R' and R" are as hereinabove defined and halide may be chloro or bromo. The free bases of (IX) or (X) may be employed or acid addition salts thereof, preferably the hydrochloride, in the presence of an acid acceptor. Suitable acid acceptors may be pyridine, triethylamine (or any suitable tertiary amine), alkali metal carbonates such as potassium carbonate and sodium carbonate, strong basic ion-exchange resins, and aqueous alkali. The reaction may be run from about 0° to 100° C, and, preferably, at 0° to 70° C until the desired reaction is complete. The isocyanate or carbamoyl halide is generally used in equimolar amounts but it may be used in excess.

Suitable organic solvents for the above reactions include aprotic aromatic solvents such as benzene, toluene and xylene; chlorinated hydrocarbon solvents such as methylene chloride, chloroform and dichloroethane; ethers such as tetrahydrofuran, diethyl ether, dimethoxyethane, diethylene glycol dimethyl ether and dioxane; ketones such as acetone, methyl ethyl ketone, methyl butyl ketone, methyl isobutyl ketone; or mixtures of said solvents. The above reactions may be graphically illustrated as follows:

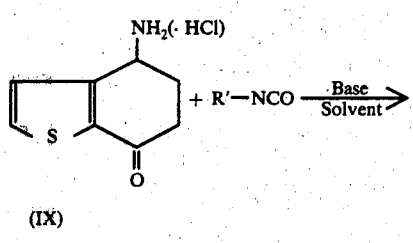

(IX)

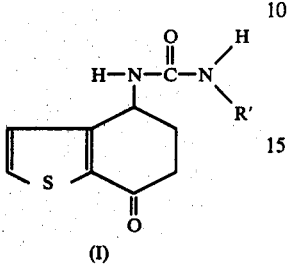

(I)

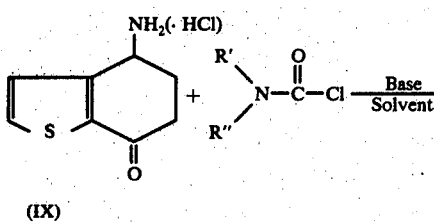

(IX)

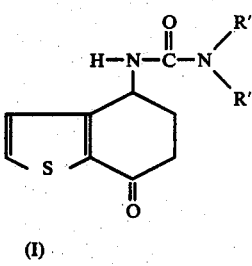

(I)

or

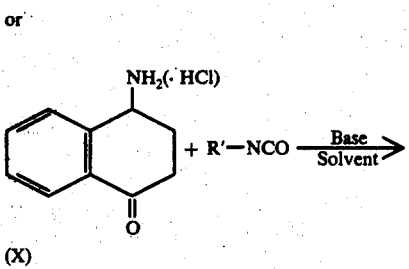

(X)

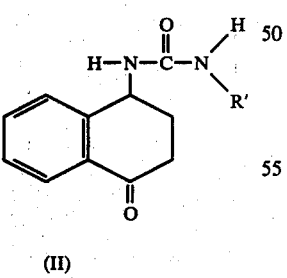

(II)

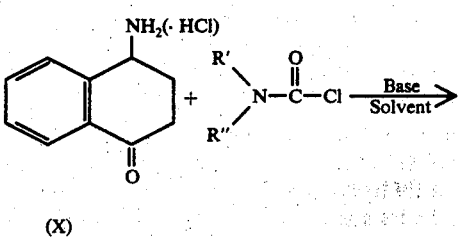

(X)

-continued

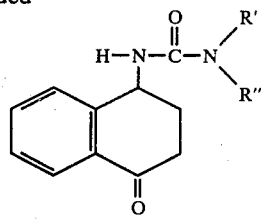

(II)

wherein R' and R" are as hereinabove defined.

All of the hereinbefore described preparations of 4,5,6,7-tetrahydro-7-oxobenzo[b]thiophene-, and 1,2,3,4-tetrahydro-4-oxonaphthalene derivatives yield racemic (dl) mixtures. Should the optically active isomers of the above compounds be desired, these may be obtained by the resolution of the racemic (dl) formulae (IX) and (X) compounds, and using the thus obtained optically active isomers in subsequent reactions.

As stated above, formulae (I) and (II) compounds are useful as growth-promoting agents for animals such as poultry, fur-bearing and farm animals, and the use of said compounds for this purpose provides the added advantage of improving feed conversion for said animals. The term "feed conversion" means the ratio of unit weight of feed per unit weight of gain and improvement in feed conversion means increased weight gain from a given unit of feed consumed.

A growth-promoting amount of a formula (I) or a formula (II) compound or an optically active isomers thereof is administered to a host animal in, or with, the animal's feed. Said compound may also be administered as a subcutaneous implant under the skin of said animal or as a parenteral injection. When administered in the feed of said animals, usually about 0.0001 to about 0.08% by weight, and preferably 0.001 to 0.04% by weight of formula (I) or formula (II) urea, is effective for increasing growth rate and improving feed conversion. When administered as a parenteral injection or subcutaneous implant, usually in amounts that will supply about 0.0005 mg to about 0.2 mg, preferably 0.001 mg to 0.1 mg/kg of body weight per day of the active compound, it will produce the desired improvement in weight gain and enhance feed conversion.

The invention is further illustrated by the non-limiting examples set forth below.

EXAMPLE 1

Preparation of 2-(2-thienyl)-1,3-dithiolane-2-propionic acid

Ethanedithiol (18.8 ml) is added to a stirred solution of 4-(2-thienyl)-4-oxobutyric acid (18.4 g) in 100 ml of 1% BF$_3$-methanol in acetic acid. The mixture is stirred for 2 days in an oil bath kept at 110° to 120° C. The mixture is then poured on ice, stirred for 1 hour, and is filtered. The filter cake is washed with water (400 ml), and is dried. The dry filter cake is dissolved in methylene chloride (200 ml) and the solution dried over magnesium sulfate. The solution is then filtered and evaporated to dryness *in vacuo* to afford 25.1 g of title compound. Recrystallization from a methylene chloride - hexane mixture affords 18.8 g of title compound, m.p. 55° to 64° C.

Similarly, substitution of 1,2-propanedithiol in place of ethanedithiol affords 4-methyl-2-(2-thienyl)-1,3-dithiolane-2-propionic acid. The use of 2,3-butanedithiol affords 4,5-dimethyl-2-(2-thienyl)-1,3-dithiolane-2-propionic acid, respectively.

In the same manner, 4-phenyl-4-oxobutyric acid is converted to 2-phenyl-1,3-dithiolane-2-propionic acid using ethanedithiol; while the use of 1,2-propanedithiol and 2,3-butanedithiol affords 4-methyl- and 4,5-dimethyl-2-phenyl-1,3-dithiolane-2-propionic acid, respectively.

EXAMPLE 2

Preparation of Spiro[benzo[b]thiophen-7(6H), 2'-[1,3]dithiolan]-4(5H)-one

Oxalyl chloride (2.54 g, 1.7 ml., 0.02 mole) is added to a stirred solution of 2-(2-thienyl)-1,3-dithiolane-2-propionic acid (3.5 g, 0.0135 mole) in dry benzene (175 ml) under a nitrogen atmosphere. The solution is stirred at room temperature for 5.25 hours and is then evaporated to dryness to yield the acid chloride as a gold oil. The infrared spectrum exhibits absorption at 1785 cm$^{-1}$.

The above acid chloride is dissolved in dry methylene chloride (175 ml) and the solution added over a period of 1.3 hours, under a nitrogen atmosphere, at 4° C to a stirred solution of stannic chloride (7.02 g, 3.15 ml, 0.027 mole) in dry methylene chloride (350 ml), while maintaining the temperature in an ice bath. After the addition is completed, the reaction mixture is stirred for 25 minutes then ice and water (ca 300 ml) are added and the mixture stirred for 30 minutes. The organic phase is separated, washed with water, aqueous sodium carbonate solution, water and saturated salt solution. The organic solution is then dried over magnesium sulfate and evaporated to dryness to afford 2.8 g of title compound as an oily solid. The infrared spectrum exhibits absorption at 1655 cm$^{-1}$ and the nmr spectrum shows two aromatic doublets at 7.13 δ and 7.27 δ (J = 5.5 Hz).

Under the same conditions, thionyl chloride and a trace of DMF in place of oxalyl chloride also gives the title compound after cyclization.

In the same manner, 4-methyl-2-(2-thienyl)-1,3-dithiolane-2-propionic acid and 4,5-dimethyl-2-(2-thienyl)-1,3-dithiolane-2-propionic acid are converted to spiro[benzo-b]thiophene-7(6H), 4'-methyl-2'-[1,3]dithiolan]-4[5H]-one and spiro[benzo[b]thiophene-7(6H), 4',5'-dimethyl-2'-[1,3]-dithiolan]-4[5H]-one, respectively.

Also in the same manner, spiro[naphthalene-4(3H), 2'-[1,3]dithiolan]-1(2H)-one, spiro[naphthalene-4(3H), 4'-methyl-2'[1,3]dithiolan]-1(2H)-one and spiro[naphthalene-4(3H), 4',5'-dimethyl-2'-[1,3-dithiolan]-1(2H)-one are prepared from their corresponding 2-phenyl-1,3-dithiolane-2-propionic acids.

EXAMPLE 3

Preparation of N-(5,6-dihydrospiro[benzo[b]thiophen-7(4H), 2'-[1,3]dithiolan]-4-yl)formamide A mixture of spiro[benzo[b]thiophene-7(6H), 2'-[1,3-dithiolan]-4(5H)-one (2.8 g), 98% formamide (4.8 ml) and formic acid (2.26 ml) is stirred and heated overnight in an oil bath kept at 130° C to 140° C. The reaction mixture is poured into water and extracted with chloroform (100 ml). The chloroform extract is washed with water and saturated salt solution and dried over magnesium sulfate. The solution is then evaporated to dryness to afford 2.6 g of red-black oil. The oil is stirred with methanol (125 ml), the supernatant is decanted and evaporated to dryness to afford 1.5 g of crude title formamide as an orange oil.

Similarly, spiro[benzo[b]thiophene-7(6H), 4'-methyl-2'-[1,3]dithiolan]-4[5H]-one is converted to N-(5,6-dihydrospiro[benzo[b]thiophene-7(4H), 4'-methyl-2'-[1,3]dithiolan]-4-yl)formamide, while spiro[benzo[b]thiophene-7(6H), 4',5'-dimethyl-2'-[1,3]dithiolan]-4[5H]-one is converted to N-(5,6-dihydrospiro[benzo[b]thiophene-7(4H), 4',5'-dimethyl-2'[1,3]dithiolan]-4-yl)formamide.

Substitution of the corresponding 1,2,3,4-tetrahydronaphtahlene compounds instead of the above-mentioned benzo[b]thiophene compounds afford N-(2,3-dihydrospiro-[naphthalene-4(3H), 2'-[1,3]dithiolan]-4-yl)formamide, N-(2,3-dihydrospiro[naphthalene-4(3H), 4'-methyl 2'-[1,3]-dithiolan]-4-yl)formamide and N-(2,3-dihydrospiro[naphthalene-4(3H), 4',5'-dimethyl-2'-[1,3]dithiolan]-4-yl)formamide.

EXAMPLE 4

Preparation of N-(4,5,6,7-tetrahydro-7-oxobenzo[b]thien-4-yl)-formamide

To a stirred mixture of N-(5,6-dihydrospiro[benzo[b]thiophen-7(4H), 2'-[1,3]dithiolan]-4-yl)formamide (1.5 g), acetonitrile (20 ml) and water is added calcium carbonate (1.65 g) and mercuric chloride (3.0 g). The mixture is stirred at room temperature for 35 minutes and acetonitrile is added. The solid is filtered and washed with acetonitrile. The filtrate (100 ml) is evaporated to dryness to afford the title compound.

Similarly, N-(5,6-dihydrospiro[benzo[b]thiophene-7(4H), 4'-methyl-2'-[1,3]dithiolan]-4-yl)formamide and N-(5,6-dihydrospiro[benzo[b]thiophene-7(4H), 4',5'-dimethyl-2'-[1,3]dithiolan]-4-yl)formamide are converted to the title compound.

Also in the same manner, N-(2,3-dihydrospiro[naphthalene-4(3H), 2'-[1,3]dithiolan]-4-yl)formamide, N-(2,3-dihydrospiro[naphthalene-4(3H), 4'-methyl-2'[1,3]-dithiolan]-4-yl)formamide and N-(2,3-dihydrospiro)-naphthalene-4(3H), 4'5'-dimethyl-2'-[1,3]dithiolan]-4-yl)formamide are converted to N-(1,2,3,4-tetrahydro-4-oxo1-naphthyl)formamide.

EXAMPLE 5

Preparation of 4,5,6,7-Tetrahydro-7-oxobenzo[b]thien-4-ylurea

A mixture of the keto-formamide of Example 4, ethyl alcohol (25 ml) and 2N hydrochloric acid (25 ml) is heated at reflux for 4 hours. The mixture is filtered and the solid washed with water. The filtrate is evaporated to dryness, the oily residue is dissolved in 50 ml of water and filtered. To the aqueous solution of the amine hydrochloride is added a solution of potassium cyanate (1.0 g) in water (5 ml) and the mixture stirred at room temperature overnight. The solid is filtered, washed well with water and air dried to afford 0.59 g of 4,5,6,7-tetrahydro-7-oxobenzo[b]thien-4-ylurea, m.p. 228° to 230° C (dec).

EXAMPLE 6

Preparation of 1,2,3,4-Tetrahydro-4-oxo-1-naphthylurea

A solution of N-(1,2,3,4-tetrahydro-4-oxo-1-naphthyl)formamide (11.0 g) in a mixture of 95% ethanol (120 ml) and 2N hydrochloric acid (120 ml) is heated at reflux for 3 hours and then stirred at room temperature overnight. The solution is filtered and concentrated in vacuo to afford a brownish-red solid. About 120 ml of ethanol is added to the solid and the mixture is then further concentrated in vacuo to yield 11.3 g of solid. This solid is added to 60 ml of water and filtered. The insoluble residue is washed with 16 ml of water, the aqueous fractions are combined, stirred and a solution of potassium cyanate in 24 ml of water added dropwise. The mixture is stirred overnight, the precipitated brown solid collected and washed with water then with cold methanol to afford 10.4 g of title compound, a grayish-brown solid, m.p. 235° to 238° C (dec).

EXAMPLE 7

Mouse Growth Regulant Tests

CFI female mice from Carworth Farm are received when they are six weeks old. They are housed 10 to a cage in air-conditioned rooms (72°–76° F) with automatically controlled lights, 14 hours on and 10 hours off. The basal diet used in these studies is Purina Laboratory Chow (see description below), which is supplied *ad libitum*. Water is also allowed *ad libitum*.

Thirteen days after arrival, the mice are weighed in groups of 10 and assigned at random to the different treatments. The concentration of the different compounds in the diet is indicated in the following Table. Twelve days later the mice are weighed again and the experiment terminated. At least three cages (30 mice) of untreated controls are included in each test. Test data are provided in Table I below, wherein data are reported as percent weight gain over controls. The following is a description of the diet to which the growth-promoting compounds are added.

DIET

| GUARANTEED ANALYSIS | |
|---|---|
| Crude protein not less than | 23.0% |
| Crude fat not less than | 4.5% |
| Crude fiber not more than | 6.0% |
| Ash not more than | 9.0% |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin,

DIET-continued vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide.

Table I

Effectiveness of 4,5,6,7-Tetrahydro-7-oxobenzo[b]thien-4-yl-urea and 1,2,3,4-Tetrahydro-4-oxo-1-naphthylurea as Animal Growth Promoting Agents Reported as Percent Weight Gain Over Controls Using Mice as the Test Animal

| Compound | Rate ppm in Diet | % Weight Gain Over Controls |
|---|---|---|
| 4,5,6,7-Tetrahydro-7-oxo-benzo[b]thien-4-ylurea | 200 | 117 |
| 1,2,3,4-Tetrahydro-4-oxo-1-naphthylurea | 50 | 35.71 |
|  | 100 | 97.40 |
|  | 200 | 93.51 |

We claim
1. A 1,3-dithiolane compound of formula:

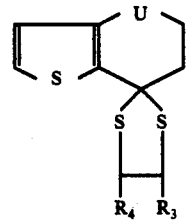

wherein $R_3$ and $R_4$ are each hydrogen or methyl; and U is the substituent

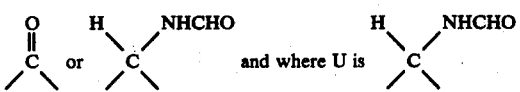

said compound is the racemic mixture and the optical isomers thereof.

2. The compound according to claim 1, spiro{benzo[b]thiophen-7(6H), 2'-[1,3]dithiolan}-4(5H)-one.

3. The compound according to claim 1, racemic N-{5,6-dihydrospiro[benzo[b]thiophen-7(4H), 2'-[1,3]dithiolan]-4-yl}formamide and the optical isomers thereof.

* * * * *